United States Patent
Schmitt et al.

(10) Patent No.: US 7,396,939 B2
(45) Date of Patent: Jul. 8, 2008

(54) 3-CYCLOPROPYL-4-(3-AMINO-2-METHYL-BENZOYL)PYRAZOLES AND THEIR USE AS HERBICIDES

(75) Inventors: Monika Schmitt, Frankfurt am Main (DE); Lothar Willms, Hofheim (DE); Ines Heinemann, Hofheim (DE); Andreas Van Almsick, Karben (DE); Thomas Auler, Leichlingen (DE); Martin Hills, Idstein (DE); Heinz Kehne, Hofheim (DE); Dieter Feucht, Eschborn (DE)

(73) Assignee: Bayer CropScience GmbH (DE)

( * ) Notice: Subject to any disclaimer, the term of this patent is extended or adjusted under 35 U.S.C. 154(b) by 391 days.

(21) Appl. No.: 11/297,677

(22) Filed: Dec. 8, 2005

(65) Prior Publication Data

US 2006/0128568 A1    Jun. 15, 2006

(30) Foreign Application Priority Data

Dec. 9, 2004    (DE) ................. 10 2004 059 302

(51) Int. Cl.
*C07D 231/10*    (2006.01)
(52) U.S. Cl. ............... 548/369.4; 548/356.1; 548/366.1
(58) Field of Classification Search .............. 548/356.1, 548/366.1, 369.4
See application file for complete search history.

(56) References Cited

U.S. PATENT DOCUMENTS 5,824,802 A    10/1998    Benko et al.
5,962,690 A *  10/1999    Benko et al. ................. 546/221
6,872,691 B2 * 3/2005    Schmitt et al. .............. 504/282

FOREIGN PATENT DOCUMENTS

| JP | 11-292849 | 10/1999 |
| WO | WO-97/41106 | 11/1997 |
| WO | WO-2005/097754 | 10/2005 |

OTHER PUBLICATIONS

European Patent Office—Patent Abstracts of Japan, English language abstract of JP-11-292849.

* cited by examiner

*Primary Examiner*—Golam M. M. Shameem
(74) *Attorney, Agent, or Firm*—Connolly Bove Lodge & Hutz LLP

(57) ABSTRACT

What is described are 3-cyclopropyl-4-(3-amino-2-methyl-benzoyl)pyrazoles of the formula (I) and their use as herbicides.

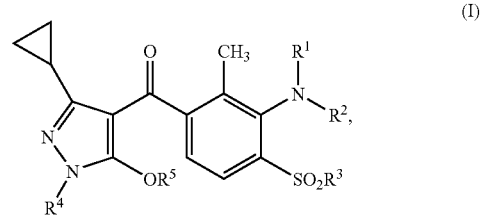

(I)

In this formula (I), $R^1$, $R^2$, $R^3$, $R^4$ and $R^5$ are various radicals.

5 Claims, No Drawings

3-CYCLOPROPYL-4-(3-AMINO-2-METHYL-BENZOYL)PYRAZOLES AND THEIR USE AS HERBICIDES

DESCRIPTION

The invention pertains to the technical field of herbicides, particularly to that of herbicides for the selective control of broad-leaved weeds and weed grasses in crops of useful plants.

From various publications, it is already known that certain benzoylpyrazoles having an amino substituent in the 3-position of the benzoyl ring have herbicidal properties. Thus, JP 11 292849 describes 3-alkyl-4-(3-aminobenzoyl)pyrazoles whose amino group is substituted by various radicals.

U.S. Pat. No. 5,824,802 also describes benzoylpyrazoles having an amino substituent in the 3-position of the benzoyl ring.

The compounds known from these publications, however, frequently do not exhibit sufficient herbicidal activity and/or sufficient compatibility with crop plants. In particular, the compounds disclosed in these publications exhibit insufficient compatibility with important crop plants such as corn, rice, cereals and soybeans.

It is an object of the present invention to provide herbicidally active compounds having herbicidal properties which are improved—improved, that is, over those of the prior art compounds—and having improved compatibility with important crop plants, in particular with corn, rice, cereals and soybeans.

It has now been found that certain 3-cyclopropyl-4-(3-amino-2-methyl-benzoyl)pyrazoles are particularly suitable as herbicides. Accordingly, the present invention provides compounds of the formula (I) and salts thereof

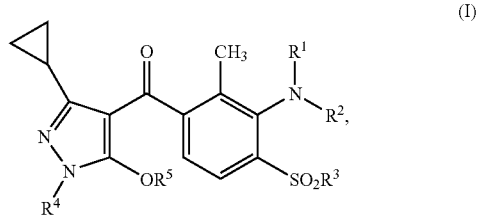

(I)

in which $R^1$ and $R^2$ independently of one another are hydrogen, furan-2-yl, tetrahydrofuran-2-yl-methyl, or $(C_1-C_4)$-alkyl, $(C_3-C_4)$-alkenyl, $(C_3-C_4)$-alkynyl, $(C_3-C_6)$-cycloalkyl, $(C_3-C_6)$-cycloalkyl-$(C_1-C_4)$-alkyl or $(C_3-C_6)$-cycloalkenyl-$(C_1-C_4)$-alkyl substituted by m radicals from the group consisting of fluorine, chlorine, bromine, cyano, hydroxyl, $(C_1-C_4)$-alkyl, $(C_1-C_4)$-alkoxy and $(C_1-C_4)$-alkoxy-$(C_1-C_4)$-alkoxy, where $R^1$ and $R^2$ are not simultaneously hydrogen, or $NR^1R^2$ is a 4- to 7-membered saturated, partially saturated, fully unsaturated or aromatic ring comprising as ring atoms n heteroatoms from the group consisting of nitrogen, oxygen and sulfur which ring is substituted by m radicals from the group consisting of fluorine, chlorine, bromine, iodine, cyano, hydroxyl, trifluoromethyl, nitro, $(C_1-C_4)$-alkyl, $(C_1-C_4)$-alkoxy, fluoro-$(C_1-C_3)$-alkyl, fluoro-$(C_1-C_3)$-alkoxy or $(C_1-C_3)$-alkoxymethyl;

$R^3$ is methyl, ethyl or isopropyl;

$R^4$ is $(C_1-C_4)$-alkyl, $(C_3-C_4)$-alkenyl or $(C_3-C_4)$-alkynyl;

$R^5$ is hydrogen, $(C_1-C_4)$-alkylsulfonyl, $(C_3-C_4)$-alkenylsulfonyl, $(C_3-C_4)$-alkynylsulfonyl, or phenylsulfonyl or benzyl substituted by m radicals from the group consisting of fluorine, chlorine, bromine, cyano, trifluoromethyl, nitro, methyl, ethyl, methoxy and ethoxy, m is 0, 1, 2 or 3;

n is 1, 2 or 3.

If $R^5$ is hydrogen, the compounds of the formula (I) according to the invention may occur in different tautomeric structures, depending on external conditions such as solvents and pH:

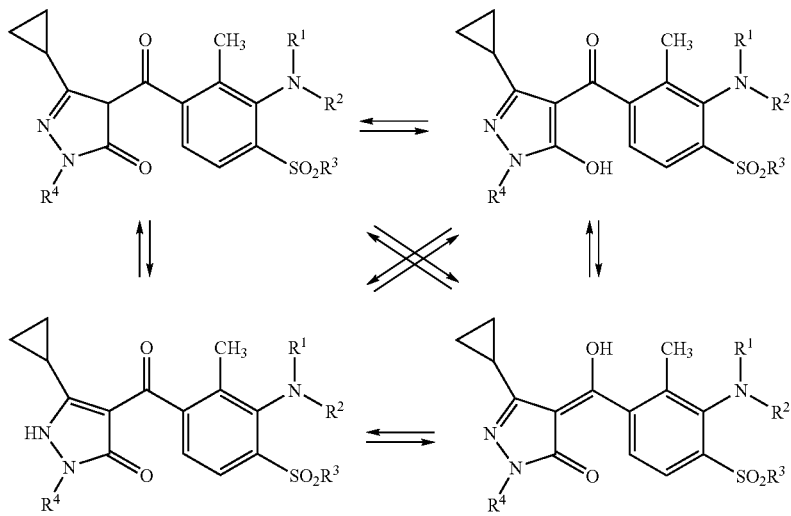

Depending on the nature of the substituents the compounds of the formula (I) contain an acidic proton, which can be removed by reaction with a base. Examples of suitable bases include hydrides, hydroxides and carbonates of lithium, sodium, potassium, magnesium and calcium, and also ammonia and organic amines such as triethylamine and pyridine. Such salts are likewise provided by the invention.

In formula (I) and all subsequent formulae it is possible for alkyl radicals having more than two carbon atoms to be straight-chain or branched. Alkyl radicals are for example methyl, ethyl, n-propyl or isopropyl, n-, iso-, t- or 2-butyl, pentyls and hexyls, such as n-hexyl, isohexyl and 1,3-dimethylbutyl. Halogen is fluorine, chlorine, bromine or iodine. Tosyl is 4-methylphenylsulfonyl.

In unsaturated radicals such as alkenyl and alkynyl, the multiple bond may be in any position of the radical. Thus, for example, the radical propynyl may be 1-propynyl or 2-propynyl.

Where a group is substituted more than once by radicals this means that this group is substituted by one or more identical or different radicals from among those specified.

Depending on the nature and linking of the substituents, the compounds of the formula (I) may be in the form of stereoisomers. Where, for example, there are one or more asymmetric carbon atoms present, enantiomers and diastereomers may occur. Stereoisomers can be obtained from the as-prepared mixtures by standard separation methods, such as by chromatographic separation methods, for example. Likewise, stereoisomers can be prepared selectively by using stereoselective reactions and employing optically active starting materials and/or auxiliaries. The invention also provides all stereoisomers and mixtures thereof that, while embraced by the formula (I), have not been defined specifically.

The 4- to 7-membered ring formed by the group $NR^1R^2$ is in particular 1-pyrrolidinyl, 2-isoxazolidinyl, 2-isothioazolidinyl, 1-pyrazolidinyl, 3-oxazolidinyl, 3-thiazolidinyl, 1-imidazolidinyl, 1,2,4-oxadiazolidin-2-yl, 1,2,4-oxadiazolidin-4-yl, 1,2,4-thiadiazolidin-2-yl, 1,2,4-thiadiazolidin-4-yl, 1,2,4-triazolidin-1-yl, 1,2,4-triazolidin-2-yl, 1,3,4-oxazolidin-3-yl, 1,3,4-thiadiazolidin-3-yl, 1,3,4-triazolidin-3-yl, 2,3-dihydropyrrol-1-yl, 2,5-dihydropyrrol-1-yl, 2,3-dihydroisoxazol-2-yl, 2,5-dihydroisoxazol-2-yl, 2,3-dihydroisothiazol-2-yl, 2,5-dihydroisothiazol-2-yl, 2,3-dihydrooxazol-3-yl, 2,3-dihydrothiazol-3-yl, 2,3-dihydroimidazol-3-yl, 2,5-dihydroimidazol-3-yl, 1-morpholinyl, 1-piperidinyl, 1-tetrahydropyridazinyl, 1-tetrahydropyrimidinyl, 1-tetrahydropyrazinyl, tetrahydro-1,3,5-triazin-1-yl, tetrahydro-1,2,4-triazin-1-yl, tetrahydro-1,2,4-triazin-2-yl, 1,3-dihydrooxazin-2-yl, 1-pyrrolyl, 1-pyrazolyl, 3-imidazolyl, 1,2,4-triazolyl-1-yl, 1,3,4-triazol-1-yl, 1-piperidine, 1-morpholinyl, 1-piperazinyl and 1,4-diazepane (homopiperazine), 1,4-oxazepane (homomorpholine), 1,4-thiazepane, 1,2,5-triazepane, 1,2-oxazepane, 1,2-thiazepane, 1,2-thiazepane 1-oxide, 1,2-thiazepane 1,1-dioxide.

Of more interest are compounds of the formula (I) in which $R^1$ and $R^2$ independently of one another are hydrogen, or $(C_1-C_4)$-alkyl, $(C_3-C_4)$-alkenyl, $(C_3-C_4)$-alkynyl, $(C_3-C_6)$-cycloalkyl, $(C_3-C_6)$-cycloalkyl-$(C_1-C_4)$-alkyl or $(C_3-C_6)$-cycloalkenyl-$(C_1-C_4)$-alkyl substituted by m radicals from the group consisting of fluorine, chlorine, bromine, cyano, hydroxyl, $(C_1-C_4)$-alkyl, $(C_1-C_4)$-alkoxy and $(C_1-C_4)$-alkoxy-$(C_1-C_4)$-alkoxy, where $R^1$ and $R^2$ are not simultaneously hydrogen, or $NR^1R^2$ is a 4- to 7-membered saturated, partially saturated, fully unsaturated or aromatic ring comprising as ring atoms n heteroatoms from the group consisting of nitrogen, oxygen and sulfur which ring is substituted by m radicals from the group consisting of fluorine, chlorine, bromine, iodine, cyano, trifluoromethyl, nitro, $(C_1-C_4)$-alkyl, $(C_1-C_4)$-alkoxy, fluoro-$(C_1-C_3)$-alkyl, fluoro-$(C_1-C_3)$-alkoxy or $(C_1-C_3)$-alkoxymethyl;

and the other substituents and indices are as defined above.

Preference is given to compounds of the formula (I) in which $R^1$ and $R^2$ independently of one another are hydrogen, methyl, butyl, ethyl, propyl, propenyl, propynyl, cyclopropyl, cyclopropylmethyl, methoxyethyl, methoxypropyl, 2-methoxy-1-methylethyl, 2-ethoxy-1-methylethyl, hydroxyethyl or ethoxyethyl, or $NR^1R^2$ form a radical from the group consisting of 1-pyrrolyl, 1-pyrrolidinyl, 1-pyrazolyl, 1-piperidine, 1-morpholinyl and 1-piperazinyl which is substituted by m radicals from the group consisting of fluorine, chlorine, bromine, iodine, cyano, trifluoromethyl, $(C_1-C_4)$-alkyl and $(C_1-C_4)$-alkoxy, and the other substituents and indices are as defined above.

Particular preference is given to compounds of the formula (I) in which $R^1$ and $R^2$ independently of one another are hydrogen, methyl, butyl, ethyl, propyl, propenyl, propynyl, cyclopropyl, cyclopropylmethyl, methoxyethyl, methoxypropyl, 2-methoxy-1-methylethyl, 2-ethoxy-1-methylethyl, hydroxyethyl or ethoxyethyl, or $NR^1R^2$ form a radical from the group consisting of 1-pyrrolyl, 1-pyrrolidinyl, 1-pyrazolyl, 1-piperidine, 1-morpholinyl and 1-piperazinyl;

$R^5$ is hydrogen, propylsulfonyl, tosyl or 2,6-difluorobenzyl, and the other substituents and indices are as defined above.

Very particular preference is given to compounds of the formula (I) in which $R^3$ is methyl or ethyl;

$R^4$ is methyl or ethyl;

$R^5$ is hydrogen, and the other substituents and indices are as defined above.

In all formulae specified below, the substituents and symbols, unless defined otherwise, have the same definition as described under formula (I).

Compounds according to the invention in which $R^5$ is hydrogen can be prepared, for example, according to the process shown in scheme 1 and known from DOS 25 13 750 by base-catalyzed reaction of a benzoyl halide with a pyrazolone or according to the process shown in scheme 2 and known, for example, from EP-A 0 186 117 by base-catalyzed reaction of a benzoyl halide with a pyrazolone and subsequent rearrangement in the presence of a base such as triethylamine and a cyanide source such as acetone cyanohydrin, trimethylsilyl cyanide or potassium cyanide.

Scheme 1

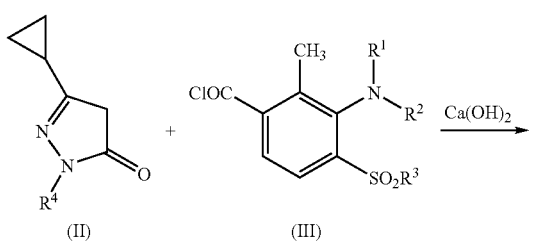

-continued

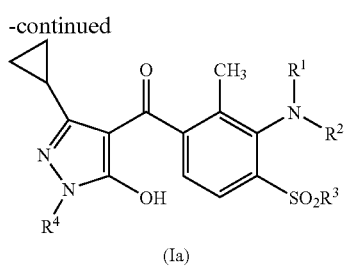
(Ia)

The starting materials used in the above schemes are either commercially available or can be prepared by methods known per se. The pyrazolones of the formula (II) used in the above schemes can be prepared according to the methods known from WO 97/41106.

The benzoyl halides of the formula (III) can be prepared according to methods known per se from the corresponding benzoic acids (IIIa) using a suitable halogenating agent such as oxalyl chloride or thionyl chloride.

The benzoic acids of the formula (IIIa) can be prepared, for example, from the corresponding 3-fluoro-substituted benzoic acids of the formula (V) by reacting them under suitable Scheme 2

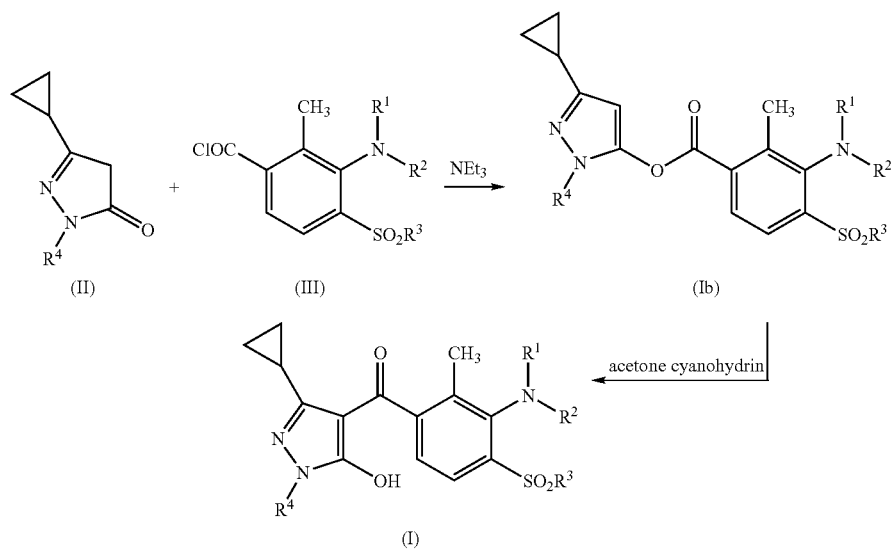

The compounds of the formula (Ib) can also be prepared directly from the corresponding benzoic acids (IV) in the presence of dehydrating agents such as DCC or EDAC. These methods are known to the person skilled in the art.

According to Scheme 3, compounds according to the invention in which $R^5$ is not hydrogen are expediently prepared from the compounds obtainable according to Scheme 1 or 2 by base-catalyzed reaction with a suitable acylating agent $R^5$—X in which X is a leaving group such as halogen. Such methods are known, for example, from DOS 25 13 750.

Scheme 3

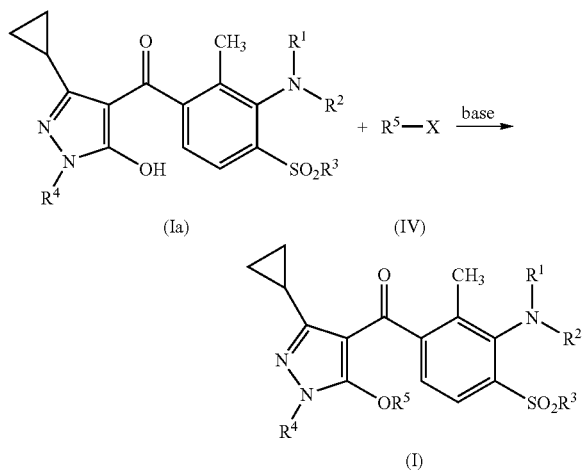

conditions with the corresponding amines $HNR^1R^2$ (Scheme 4). Suitable conditions are, for example, several hours of heating in an excess of the amine. Such reactions are known to the person skilled in the art.

Scheme 4

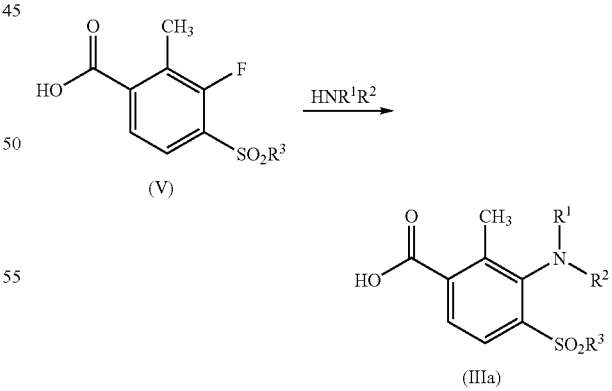

Furthermore, even after its introduction the group —$NR^1R^2$ can be derivatized further, for example by reductive amination.

According to Scheme 5, 4-alkylsulfonyl-3-fluoro-2-methylbenzoic acids of the formula (VI) can be obtained from 4-chloro-3-fluoro-2-methylbenzoic acids (VII) or esters thereof by reaction with sodium alkoxides and subsequent oxidation with a suitable oxidizing agent. Suitable oxidizing agents are, for example, hydrogen peroxide in glacial acetic acid or 3-chloroperbenzoic acid.

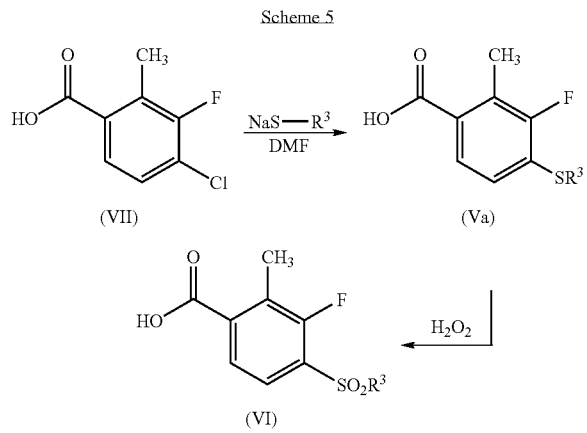

Scheme 5

4-Chloro-3-fluoro-2-methylbenzoic acid (VII) is known and can be prepared, for example, by the method described in U.S. Pat. No. 5,334,753.

The compounds of the formula (I) according to the invention have an excellent herbicidal activity against a broad spectrum of economically important monocotyledonous and dicotyledonous weed plants. The active substances provide effective control even of perennial weeds which produce shoots from rhizomes, root stocks or other perennial organs and which cannot be easily controlled. In this context, it generally does not matter whether the substances are applied before sowing, pre-emergence or post-emergence. Some representatives of the monocotyledonous and dicotyledonous weed flora which can be controlled by the compounds according to the invention may be mentioned individually as examples, but this is not to be taken to mean a restriction to certain species. The monocotyledonous weed species which are controlled well are, for example, *Avena, Lolium, Alopecurus, Phalaris, Echinochloa, Digitaria, Setaria* and *Cyperus* species from the annual group, and *Agropyron, Cynodon, Imperata* and *Sorghum* or else perennial *Cyperus* species amongst the perennial species. In the case of dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from the annual group, and *Convolvulus, Cirsium, Rumex* and *Artemisia* among the perennial weeds. Weed plants which are found under the specific culture conditions of rice, such as, for example, *Echinochloa, Sagittaria, Alisma, Eleocharis, Scirpus* and *Cyperus*, are also controlled outstandingly well by the active substances according to the invention. If the compounds according to the invention are applied to the soil surface prior to germination, then either emergence of the weed seedlings is prevented completely, or the weeds grow until they have reached the cotyledon stage but growth then comes to a standstill and, after a period of three to four weeks, the plants eventually die completely. When the active substances are applied post-emergence to the green parts of the plants, growth also stops drastically very soon after the treatment, and the weeds remain at the growth stage of the time of application, or, after a certain period of time, they die completely so that in this way competition by the weeds, which is detrimental for the crop plants, is thus eliminated at a very early stage and in a sustained manner. In particular, the compounds according to the invention have an outstanding action against *Apera spica venti, Chenopodium album, Lamium purpureum, Polygonum convulvulus, Stellaria media, Veronica hederifolia, Veronica persica, Viola tricolor* and also against *Amaranthus, Galium* and *Kochia* species.

The compounds according to the invention have an outstanding herbicidal activity against monocotyledonous and dicotyledonous weeds, and yet crop plants of economically important crops such as, for example, wheat, barley, rye, rice, corn, sugar beet, cotton and soybean suffer only negligible damage, if any. In particular, they are outstandingly well tolerated in corn, rice, cereals and soybean. This is why the present compounds are highly suitable for the selective control of unwanted vegetation in stands of agricultural useful plants or of ornamentals.

Owing to their herbicidal properties, these compounds can also be employed for controlling weed plants in crops of genetically modified plants which are known or are yet to be developed. As a rule, the transgenic plants are distinguished by particularly advantageous properties, for example by resistances to certain pesticides, especially certain herbicides, by resistances to plant diseases or causative organisms of plant diseases, such as certain insects or microorganisms such as fungi, bacteria or viruses. Other particular properties concern for example the harvested material with regard to quantity, quality, shelf life, composition and specific constituents. Thus, transgenic plants are known which have an increased starch content or whose starch quality has been modified, or those whose fatty acid composition in the harvested material is different.

The compounds of the formula (I) according to the invention or their salts are preferably employed in economically important transgenic crops of useful plants and ornamentals, for example cereals such as wheat, barley, rye, oats, millet, rice, cassaya and corn, or else crops of sugar beet, cotton, soybean, oilseed rape, potato, tomato, pea and other vegetables. The compounds of the formula (I) can preferably be employed as herbicides in crops of useful plants which are resistant, or have been genetically modified to be resistant, to the phytotoxic effects of the herbicides, in particular soybean and corn.

Conventional routes for the generation of novel plants which have modified properties compared with existing plants are, for example, traditional breeding methods and the generation of mutants. Alternatively, novel plants with modified properties can be generated with the aid of recombinant methods (see, for example, EP-A-0221044, EP-A-0131624). For example, several cases of the following have been described:

recombinant modifications of crop plants for the purposes of modifying the starch synthesized in the plants (e.g. WO 92/11376, WO 92/14827, WO 91/19806), transgenic crop plants which exhibit resistances to certain herbicides of the glufosinate type (cf. e.g. EP-A-0242236, EP-A-0242246), glyphosate type (WO 92/00377) or of the sulfonylurea type (EP-A-0257993, U.S. Pat. No. 5,013,659), transgenic crop plants, for example cotton, with the ability to produce *Bacillus thuringiensis* toxins (Bt toxins), which make the plants resistant to certain pests (EP-A-0142924, EP-A-0193259), transgenic crop plants with a modified fatty acid composition (WO 91/13972), A large number of techniques in molecular biology, with the aid of which novel transgenic plants with modified properties can be generated, are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996 or Christou, "Trends in Plant Science" 1 (1996) 423-431. To carry out such recombinant manipulations, nucleic acid molecules can be introduced into plasmids which permit a mutagenesis or a sequence alteration by recombination of DNA sequences. With the aid of the abovementioned standard processes, it is possible, for example, to carry out base substitutions, to remove part sequences or to add natural or synthetic sequences. The fragments can be provided with adapters or linkers to link the DNA fragments to each other.

Plant cells with a reduced activity of a gene product can be obtained, for example, by expressing at least one corresponding antisense RNA, a sense RNA for achieving a cosuppression effect, or the expression of at least one suitably constructed ribozyme which specifically cleaves transcripts of the abovementioned gene product.

To this end, it is possible, on the one hand, to use DNA molecules which encompass all of the coding sequence of a gene product including any flanking sequences which may be present, but also DNA molecules which only encompass portions of the coding sequence, it being necessary for these portions to be so long as to cause an antisense effect in the cells. Another possibility is the use of DNA sequences which have a high degree of homology with the coding sequences of a gene product, but are not completely identical.

When expressing nucleic acid molecules in plants, the protein synthesized may be localized in any desired compartment of the plant cell. However, to achieve localization in a particular compartment, the coding region can, for example, be linked to DNA sequences which ensure localization in a particular compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give intact plants. In principle, the transgenic plants can be plants of any desired plant species, i.e. both monocotyledonous and dicotyledonous plants. Thus, transgenic plants can be obtained which exhibit modified properties owing to the overexpression, suppression or inhibition of homologous (i.e. natural) genes or gene sequences or expression of heterologous (i.e. foreign) genes or gene sequences.

When using the active substances according to the invention in transgenic crops, effects are frequently observed—in addition to the effects against weed plants to be observed in other crops—which are specific for the application in the transgenic crop in question, for example a modified or specifically widened controllable weed spectrum, modified application rates which may be employed for the application, preferably good combining ability with the herbicides to which the transgenic crop is resistant, and an effect on the growth and yield of the transgenic crop plants. The invention therefore also relates to the use of the compounds according to the invention as herbicides for controlling harmful plants in transgenic crop plants.

The substances according to the invention additionally have outstanding growth-regulatory properties in crop plants. They engage in the plants' metabolism in a regulatory fashion and can thus be employed for the targeted influencing of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops, allowing lodging to be reduced or prevented completely.

The compounds according to the invention can be employed in the form of wettable powders, emulsifiable concentrates, sprayable solutions, dusts or granules in the customary preparations. The invention therefore further relates also to herbicidal compositions comprising compounds of the formula (I). The compounds of the formula (I) can be formulated in various ways, depending on the prevailing biological and/or chemico-physical parameters. Examples of suitable formulations which are possible are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, dusts (DP), capsule suspensions (CS), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, such as butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are:

calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays such as kaolin, bentonite and pyrophyllite, or diatomaceous earth. Suspension concentrates can be water based or oil based. They can be prepared for example by wet-grinding by means of customary bead mills, if appropriate with addition of surfactants, as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of tackifiers, for example polyvinyl alcohol, sodium polyacrylate or else mineral oils. Suitable active substances can also be granulated in the fashion which is conventional for the production of fertilizer granules, if desired as a mixture with fertilizers. Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8-57. For further details on the formulation of crop protection products see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the stickers, wetters, dispersants, emulsifiers, penetrants, preservatives, antifreeze agents, solvents, fillers, carriers, colorants, antifoams, evaporation inhibitors, and pH and viscosity regulators which are conventional in each case.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

Active substances which can be employed in combination with the active substances according to the invention in mixed formulations or in a tank mix are, for example, known active substances as are described, for example, in Weed Research 26, 441-445 (1986) or "The Pesticide Manual", 13th edition, The British Crop Protection Council and the Royal Soc. of Chemistry, 2003 and literature cited therein. Known herbicides which are to be mentioned, and can be combined with the compounds of the formula (I), are, for example, the following active substances (note: the compounds are either designated by the common name according to the International Organization for Standardization (ISO) or using the chemical name, if appropriate together with a customary code number):

acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516H, i.e. 5-fluoro-2-phenyl-4H-3,1-benzoxazin-4-one; benazolin; benfluralin; benfuresate; bensulfuronmethyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; metham; methabenzthiazuron; methazole; methoxyphenone; methyldymrori; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl) phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; pinoxaden; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations, which are present in commercially available form, are, if appropriate, diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use. The required application rate of the compounds of the formula (I) varies with the external conditions such as, inter alia, temperature, humidity and the nature of the herbicide used. It can vary within wide limits, for example between 0.001 and 1.0 kg/ha or more of active substance, but it is preferably between 0.005 and 750 g/ha, in particular between 0.005 and 250 g/ha.

The examples which follow illustrate the invention.

A. CHEMICAL EXAMPLES

1. Preparation of (3-cyclopropyl-5-hydroxy-1-methyl-1H-pyrazol-4-yl)[3-[(3-methoxypropyl)amino]-2-methyl-4-(methylsulfonyl)phenyl]methanone (Example 13)

Step 1: Methyl 2-fluoro-2-methyl-4-(methylthio)benzoate 43.3 g (0.214 mol) of methyl 4-chloro-3-fluoro-2-methylbenzoate were dissolved in 250 ml of DMF, and 17.34 g (0.235 mol) of sodium thiomethoxide were added at room temperature (RT). The temperature increased to 65° C. and the mixture was stirred at a bath temperature of 50° C. for another 4 h. Most of the solvent was then removed under reduced pressure, and the residue was acidified with 10% strength $H_2SO_4$ and extracted with EA (ethyl acetate). The organic phase was dried over $MgSO_4$ and concentrated. This gave a colored oil of a purity of about 60%. crude yield: 46 g $^1$H-NMR: $\delta[CDCl_3]$ 2.47 (s,3H), 2.5 (d,3H), 3.85 (s,3H), 7.0 (t,1H), 7.65 (d,1H)

Step 2: Methyl 2-fluoro-2-methyl-4-(methylsulfonyl)benzoate

At 50° C., 58 g (0.6 mol) of 35% strength $H_2O_2$ were added slowly to 40 g of crude methyl 2-fluoro-2-methyl-4-(methylthio)benzoate in 250 ml of glacial acetic acid. The mixture was then stirred at 100° C. for another 3 h. The mixture was allowed to cool, added to 1 l of ice water and extracted repeatedly with EA. The combined organic phases were dried over $MgSO_4$ and concentrated.

Crude yield: 46.8 g, purity about 60% (HPLC) $^1$H-NMR: $\delta[CDCl_3]$ 2.5 (d,3H), 3.21 (s,3H), 3.92 (s,3H), 7.78 (m,2H)

Step 3: 2-Fluoro-2-methyl-4-(methylsulfonyl)benzoic acid 53.8 g of crude methyl 2-fluoro-2-methyl-4-(methylsulfonyl)benzoate were initially charged in 500 ml of THF, and 10.5 g NaOH dissolved in 500 ml of $H_2O$ were added. The mixture was stirred at RT for 3 h, and most of the THF was then removed under reduced pressure. The residue was washed with diethyl ether and the aqueous phase was then acidified with 10% strength $H_2SO_4$. The precipitated crystals were filtered off with suction, washed with cold water and dried. This gave colorless crystals.

Crude yield: 49.8 g, purity about 70% (HPLC) $^1$H-NMR: $\delta[CDCl_3]$ 2.52 (d,3H), 3.2 (s,3H), 7.78 (m,2H)

Step 4: 3-[(3-Methoxypropyl)amine]-2-methyl-4-(methylsulfonyl)benzoic acid 1 g of crude 2-fluoro-2-methyl-4-(methylsulfonyl)benzoic acid and 11.9 g (133 mmol) of 3-methoxypropylamine were mixed and, with stirring, heated at 120° C. for 24 h. The mixture was allowed to cool, added to 100 ml of water, acidified with 10% strength $H_2SO_4$ and extracted repeatedly with EA. The organic phases were dried over MgSO$_4$ and concentrated. This gave colorless crystals.

Crude yield: 1.07 g, purity about 88% (HPLC) $^1$H-NMR: δ[CDCl$_3$] 1.95 (m,2H), 2.52 (d,3H), 3.12 (s,3H), 3.25 (t,2H), 3.39 (s,3H), 3.58 (t,2H), 7.58 (d,2H), 7.8 (d,2H)

Step 5: (3-Cyclopropyl-5-hydroxy-1-methyl-1H-pyrazol-4-yl)[3-[(3-methoxy-propyl)amino]-2-methyl-4-(methylsulfonyl)phenyl]methanone Under nitrogen, 0.53 g of crude 3-[(3-methoxypropyl)amine]-2-methyl-4-(methylsulfonyl)benzoic acid was dissolved in 30 ml of CH$_3$CN, and 0.32 g (2 mmol) of 5-hydroxy-3-cyclopropyl-1-methylpyrazole and 0.41 g (2 mmol) of EDAC were then added. The mixture was stirred at RT for one day. 0.36 g (4 mmol) of NEt$_3$, 0.07 g (1 mmol) of Me$_3$SiCN and a spatula tip of KCN were then added, and the mixture was stirred at RT for two days. The mixture was then concentrated, and the residue was taken up in 100 ml of CH$_2$Cl$_2$ and washed with 10% strength H$_2$SO$_4$. The organic phase was dried over MgSO$_4$, concentrated and purified chromatographically (SiO$_2$, EA/n-heptane=1:1+5% acetic acid) and crystallized from diethyl ether. This gave colorless crystals.

Yield: 52 mg, (0.12 mmol) 7%, purity 96% (HPLC) $^1$H-NMR: δ[CDCl$_3$] 0.53 (m,2H), 0.78 (m,2H), 0.98 (m,1H), 1.95 (m,2H), 2.3 (s,3H), 3.1 (s,3H), 3.28 (t,2H), 3.38 (s,3H), 3.58 (t,2H), 3.6 (s,3H), 6.99 (d,1H), 7.82 (d,1H)

2. Preparation of (3-cyclopropyl-5-hydroxy-1-methyl-1H-pyrazol-4-yl)[3-[(2-methoxyethyl)(methyl)amino]-2-methyl-4-(methylsulfonyl)phenyl]methanone (Example 24)

Step 1: 3-[(2-Methoxyethyl)(methyl)amino]-2-methyl-4-(methylsulfonyl)benzoic acid Under nitrogen, 1.0 g (3 mmol) of 3-[(2-methoxyethyl)amino]-2-methyl-4-(methylsulfonyl)benzoic acid was dissolved in 150 ml of THF, and 10 g of paraformaldehyde and then, a little at a time, 0.7 g (20 mmol) of NaBH$_4$ were added. 15 ml of trifluoroacetic acid were then slowly added dropwise. The mixture was stirred at RT for another 3 days. For work-up, 10% strength H$_2$SO$_4$ was added, and the mixture was extracted repeatedly with EA and then dried over MgSO$_4$ and concentrated. This gave a brownish oil.

Crude yield: 1.2 g, purity 98% (HPLC) $^1$H-NMR: δ[CDCl$_3$] 2.52 (d,3H), 2.92 (s,3H), 3.35 (s,6H), 3.42 (m,2H), 3.65 (m,2H), 7.8 (d,2H), 7.98 (d,2H)

Step 2: (3-Cyclopropyl-5-hydroxy-1-methyl-1H-pyrazol-4-yl)[3-[(2-methoxyethyl)(methyl)amino]-2-methyl-4-(methylsulfonyl)phenyl]methanone Under nitrogen, 0.59 g of crude 3-[(2-methoxyethyl)amino]-2-methyl-4-(methylsulfonyl)benzoic acid was dissolved in 30 ml of CH$_3$CN, and 0.35 g (3 mmol) of 5-hydroxy-3-cyclopropyl-1-methylpyrazole and 0.45 g (2 mmol) of EDAC were then added. The mixture was stirred at RT for one day. 0.36 g (4 mmol) of NEt$_3$, 0.08 g (1 mmol) of Me$_3$SiCN and a spatula tip of KCN were then added, and the mixture was stirred at RT for two days. The mixture was then concentrated, and the residue was taken up in 100 ml of CH$_2$Cl$_2$ and washed with 10% strength H$_2$SO$_4$. The organic phase was dried over MgSO$_4$, concentrated and the residue was purified chromatographically (SiO$_2$, EA/n-heptane=1:1+5% acetic acid). This gave a brown oil.

Yield: 144 mg, (0.34 mmol) 16%, purity 93% (HPLC) $^1$H-NMR: δ[CDCl$_3$] 0.53 (m,2H), 0.78 (m,2H), 0.9 (m,1H), 2.35 (s,3H), 2.95 (s,3H), 3.25 (m,2H), 3.17 (s,3H), 3.18 (s,3H), 3.42 (m,2H), 3.6 (s,3H), 3.65 (m,2H), 7.32 (d,1H), 8.02 (d,1H)

The examples listed in table A below were prepared analogously to the above methods or are obtainable analogously to the above methods.

The abbreviations used have the following meanings:

Bu=butyl Et=ethyl Me=methyl Pr=propyl Ph=phenyl

TABLE A

| No. | NR$^1$R$^2$ | R$^3$ | R$^4$ | R$^5$ | $^1$H-NMR: δ[CDCl$_3$] |
|---|---|---|---|---|---|
| 1 | NHMe | Me | Me | H | 0.54(m, 2H), 0.78(m, 2H), 1.01 (m, 1H), 2.33(s, 3H), 3.00(s, 3H), 3.08 (s, 3H), 3.62(s, 3H), 7.00(d, 1H), 7.80 (d, 1H) |
| 2 | NHEt | Me | Me | H | 0.55(m, 2H), 0.77(m, 2H), 1.00 (m, 1H), 1.20(t, 3H), 2.30(s, 3H), 3.07 (s, 3H), 3.27(q, 2H), 3.59(s, 3H), 6.98 (d, 1H), 7.80(d, 1H) |
| 3 | NH(n-Pr) | Me | Me | H | 0.53(m, 2H), 0.78(m, 2H), 0.98 (m, 1H), 1.02(t, 3H), 1.7(m, 2H), 2.3 (s, 3H), 3.1(s, 3H), 3.18(t, 2H), 3.6 (s, 3H), 6.95(d, 1H), 7.8(d, 1H) |
| 4 | NH(n-Bu) | Me | Me | H | 0.53(m, 2H), 0.78(m, 2H), 0.95(t, 3H), 0.98(m, 1H), 1.45(m, 2H), 1.65 (m, 2H), 2.3(s, 3H), 3.1(s, 3H), 3.2 (t, 2H), 3.6(s, 3H), 6.95(d, 1H), 7.8 (d, 1H) |

TABLE A-continued

| No. | NR$^1$R$^2$ | R$^3$ | R$^4$ | R$^5$ | $^1$H-NMR: δ[CDCl$_3$] |
|---|---|---|---|---|---|
| 5 | NHCH$_2$CH=CH$_2$ | Me | Me | H | 0.53(m, 2H), 0.78(m, 2H), 0.98 (m, 1H), 2.3(s, 3H), 3.1(s, 3H), 3.6 (s, 3H), 3.85(d, 2H), 5.22(m, 1H), 5.35 (m, 1H), 6.0(m, 1H), 7.02(d, 1H), 7.82 (d, 1H) |
| 6 | NHCH$_2$C≡CH | Me | Me | H | |
| 7 | NHCH$_2$cPr | Me | Me | H | 0.3(m, 2H), 0.53(m, 2H), 0.6(m, 2H), 0.78(m, 2H), 0.98(m, 1H), 1.1(m, 1H), 2.3(s, 3H), 3.08(d, 2H), 3.1(s, 3H), 3.6 (s, 3H), 6.95(d, 1H), 7.81(d, 1H) |
| 8 | NH(CH$_2$)$_2$OH | Me | Me | H | 0.53(m, 2H), 0.78(m, 2H), 0.98 (m, 1H), 2.3(s, 3H), 3.2(s, 3H), 3.38 (t, 2H), 3.6(s, 3H), 3.85(t, 2H), 7.02 (d, 1H), 7.82(d, 1H) |
| 9 | NH(CH$_2$)$_2$OMe | Me | Me | H | 0.53(m, 2H), 0.78(m, 2H), 0.98 (m, 1H), 2.3(s, 3H), 3.18(s, 3H), 3.4 (t, 2H), 3.4(s, 3H), 3.6(t, 2H), 3.6 (s, 3H), 6.98(d, 1H), 7.82(d, 1H) |
| 10 | N NH(CH$_2$)$_2$OEt | Me | Me | H | 0.53(m, 2H), 0.78(m, 2H), 0.98 (m, 1H), 1.22(t, 3H), 2.3(s, 3H), 3.2 (s, 3H), 3.4(t, 2H), 3.58(q, 2H), 3.6 (s, 3H), 3.62(t, 2H), 6.95(d, 1H), 7.82 (d, 1H) |
| 11 | NHCHMeCH$_2$OMe | Me | Me | H | 0.53(m, 2H), 0.78(m, 2H), 1.02 (m, 1H), 1.22(d, 3H), 2.25(s, 3H), 3.18 (s, 3H), 3.3(s, 3H), 3.4(m, 2H), 3.6 (s, 3H), 3.82(m, 1H), 6.95(d, 1H), 7.82 (d, 1H) |
| 12 | NHCHMeCH$_2$OEt | Me | Me | H | |
| 13 | NH(CH$_2$)$_3$OMe | Me | Me | H | 0.54(m, 2H), 0.77(m, 2H), 0.99 (m, 1H), 1.94(m, 2H), 2.32(s, 3H), 3.11 (s, 3H), 3.29(t, 2H), 3.37(s, 3H), 3.55 (t, 2H), 3.60(s, 3H), 6.99(d, 1H), 7.82 (d, 1H) |
| 14 |  | Me | Me | H | 0.53(m, 2H), 0.78(m, 2H), 0.9(m, 1H), 2.05(m, 4H), 2.3(s, 3H), 3.25(s, 3H), 3.3(m, 4H), 3.6(s, 3H), 7.35(d, 1H), 8.02(d, 1H) |
| 15 |  | Me | Me | H | 0.53(m, 2H), 0.78(m, 2H), 0.9(m, 1H), 1.65-1.95(m, 6H), 2.4(s, 3H), 3.1 (m, 2H), 3.3(m, 2H), 3.35(s, 3H), 3.6 (s, 3H), 7.3(d, 1H), 8.03(d, 1H) |
| 16 | NMe$_2$ | Me | Me | H | 0.50(m, 2H), 0.77(m, 2H), 0.90 (m, 1H), 2.37(s, 3H), 2.93(s, 6H), 3.28 (s, 3H), 3.61(s, 3H), 7.33(d, 1H), 8.02 (d, 1H) |
| 17 | NMeEt | Me | Me | H | 0.51(m, 2H), 0.77(m, 2H), 0.92 (m, 1H), 1.23(t, 3H), 2.34(s, 3H), 2.87 (s, 3H), 3.07-3.37(m, 2H), 3.32(s, 3H), 3.60(s, 3H), 7.33(d, 1H), 8.04(d, 1H) |
| 18 | NMe(n-Pr) | Me | Me | H | 0.52(m, 2H), 0.78(m, 2H), 0.89 (m, 1H), 0.92(t, 3H), 1.67(m, 2H), 2.35 (s, 3H), 2.88(s, 3H), 2.93-3.18(m, 2H), 3.30(s, 3H), 3.61(s, 3H), 7.31(d, 1H), 8.03(d, 1H) |
| 19 | NMe(n-Bu) | Me | Me | H | |
| 20 | NMeCH$_2$CH=CH$_2$ | Me | Me | H | |
| 21 | NMeCH$_2$C≡CH | Me | Me | H | |

TABLE A-continued

| No. | NR¹R² | R³ | R⁴ | R⁵ | ¹H-NMR: δ[CDCl₃] |
|---|---|---|---|---|---|
| 22 | NMeCH₂cPr | Me | Me | H | 0.10-0.28(m, 2H), 0.42-0.54(m, 3H), 0.63(m, 1H), 0.76(m, 2H), 0.92 (m, 1H), 1.12(m, 1H), 2.33(s, 3H), 2.71 (m, 1H), 2.97(s, 3H), 3.28(m, 1H), 3.36 (s, 3H), 3.61(s, 3H), 7.32(d, 1H), 8.04 (d, 1H) |
| 23 | NMe(CH₂)₂OH | Me | Me | H | |
| 24 | NMe(CH₂)₂OMe | Me | Me | H | 0.50(m, 2H), 0.77(m, 2H), 0.91 (m, 1H), 2.36(s, 3H), 2.94(s, 3H), 3.20-3.28(m, 1H), 3.35(s, 3H), 3.37(s, 3H), 3.39-3.47(m, 2H), 3.61(s, 3H), 3.66 (m, 2H), 7.33(d, 1H), 8.03(d, 1H) |
| 25 | NMe(CH₂)₂OEt | Me | Me | H | 0.50(m, 2H), 0.76(m, 2H), 0.90 (m, 1H), 1.09(t, 3H), 2.37(s, 3H), 2.95 (s, 3H), 3.18-3.28(m, 1H), 3.36(s, 3H), 3.39-3.47(m, 1H), 3.50(q, 2H), 3.61 (s, 3H), 3.70(m, 2H), 7.32(d, 1H), 8.03 (d, 1H) |
| 26 | NMeCHMeCH₂OMe | Me | Me | H | |
| 27 | NMeCHMeCH₂OEt | Me | Me | H | |
| 28 | NMe(CH₂)₃OMe | Me | Me | H | 0.52(m, 2H), 0.78(m, 2H), 0.91 (m, 1H), 1.96(m, 2H), 2.36(s, 3H), 2.88 (s, 3H), 3.04-3.17(m, 1H), 3.23-3.34 (m, 1H), 3.27(s, 3H), 3.32(s, 3H), 3.37-3.47 (m, 2H), 3.60(s, 3H), 7.32(d, 1H), 8.03(d, 1H) |
| 29 | NHMe | Et | Me | H | 0.54(m, 2H), 0.78(m, 2H), 0.99 (m, 1H), 1.28(t, 3H), 2.33(s, 3H), 2.96 (s, 3H), 3.12(q, 2H), 3.61(s, 3H), 6.98 (d, 1H), 7.75(d, 1H) |
| 30 | NHEt | Et | Me | H | |
| 31 | NH(n-Pr) | Et | Me | H | |
| 32 | NH(n-Bu) | Et | Me | H | |
| 33 | NHCH₂CH=CH₂ | Et | Me | H | |
| 34 | NHCH₂C≡CH | Et | Me | H | |
| 35 | NHCH₂cPr | Et | Me | H | |
| 36 | NH(CH₂)₂OH | Et | Me | H | |
| 37 | NH(CH₂)₂OMe | Et | Me | H | |
| 38 | NH(CH₂)₂OEt | Et | Me | H | |
| 39 | NHCHMeCH₂OMe | Et | Me | H | |
| 40 | NHCHMeCH₂OEt | Et | Me | H | |
| 41 | NH(CH₂)₃OMe | Et | Me | H | |
| 42 | pyrrolidinyl | Et | Me | H | |
| 43 | piperidinyl | Et | Me | H | |
| 44 | NMe₂ | Et | Me | H | |
| 45 | NMeEt | Et | Me | H | |
| 46 | NMe(n-Pr) | Et | Me | H | |
| 47 | NMe(n-Bu) | Et | Me | H | |
| 48 | NMeCH₂CH=CH₂ | Et | Me | H | |
| 49 | NMeCH₂C≡CH | Et | Me | H | |
| 50 | NMeCH₂cPr | Et | Me | H | |
| 51 | NMe(CH₂)₂OH | Et | Me | H | |
| 52 | NMe(CH₂)₂OMe | Et | Me | H | |
| 53 | NMe(CH₂)₂OEt | Et | Me | H | |
| 54 | NMeCHMeCH₂OMe | Et | Me | H | |
| 55 | NMeCHMeCH₂OEt | Et | Me | H | |
| 56 | NHMe | Me | Et | H | |

TABLE A-continued

| No. | NR¹R² | R³ | R⁴ | R⁵ | ¹H-NMR: δ[CDCl₃] |
|---|---|---|---|---|---|
| 57 | NHEt | Me | Et | H | |
| 58 | NH(n-Pr) | Me | Et | H | |
| 59 | NH(n-Bu) | Me | Et | H | |
| 60 | NHCH₂CH=CH₂ | Me | Et | H | |
| 61 | NHCH₂C≡CH | Me | Et | H | |
| 62 | NHCH₂cPr | Me | Et | H | |
| 63 | NH(CH₂)₂OH | Me | Et | H | |
| 64 | NH(CH₂)₂OMe | Me | Et | H | 0.52(m, 2H), 0.77(m, 2H), 1.00 (m, 1H), 1.40(t, 3H), 2.31(s, 3H), 3.18 (s, 3H), 3.40(m, 5H), 3.61(m, 2H), 3.97 (q, 2H), 7.00(d, 1H), 7.83(d, 1H) |
| 65 | NH(CH₂)₂OEt | Me | Et | H | |
| 66 | NHCHMeCH₂OMe | Me | Et | H | |
| 67 | NHCHMeCH₂OEt | Me | Et | H | |
| 68 | NH(CH₂)₃OMe | Me | Et | H | |
| 69 | pyrrolidinyl | Me | Et | H | |
| 70 | piperidinyl | Me | Et | H | |
| 71 | NMe₂ | Me | Et | H | |
| 72 | NMeEt | Me | Et | H | |
| 73 | NMe(n-Pr) | Me | Et | H | |
| 74 | NMe(n-Bu) | Me | Et | H | |
| 75 | NMeCH₂CH=CH₂ | Me | Et | H | |
| 76 | NMeCH₂C≡CH | Me | Et | H | |
| 77 | NMeCH₂cPr | Me | Et | H | |
| 78 | NMe(CH₂)₂OH | Me | Et | H | |
| 79 | NMe(CH₂)₂OMe | Me | Et | H | |
| 80 | NMe(CH₂)₂OEt | Me | Et | H | |
| 81 | NMeCHMeCH₂OMe | Me | Et | H | |
| 82 | NHCHMeCH₂OEt | Me | Et | H | |
| 83 | NHMe | Et | Et | H | |
| 84 | NHEt | Et | Et | H | |
| 85 | NH(n-Pr) | Et | Et | H | |
| 86 | NH(n-Bu) | Et | Et | H | |
| 87 | NHCH₂CH=CH₂ | Et | Et | H | |
| 88 | NHCH₂C≡CH | Et | Et | H | |
| 89 | NHCH₂cPr | Et | Et | H | |
| 90 | NH(CH₂)₂OH | Et | Et | H | |
| 91 | NH(CH₂)₂OMe | Et | Et | H | |
| 92 | NH(CH₂)₂OEt | Et | Et | H | |
| 93 | NHCHMeCH₂OMe | Et | Et | H | |
| 94 | NHCHMeCH₂OEt | Et | Et | H | |
| 95 | NH(CH₂)₃OMe | Et | Et | H | |
| 96 | pyrrolidinyl | Et | Et | H | |
| 97 | piperidinyl | Et | Et | H | |
| 98 | NMe₂ | Et | Et | H | |
| 99 | NMeEt | Et | Et | H | |
| 100 | NMe(n-Pr) | Et | Et | H | |
| 101 | NMe(n-Bu) | Et | Et | H | |

TABLE A-continued

| No. | NR¹R² | R³ | R⁴ | R⁵ | ¹H-NMR: δ[CDCl₃] |
|---|---|---|---|---|---|
| 102 | NMeCH₂CH=CH₂ | Et | Et | H | |
| 103 | NMeCH₂C≡CH | Et | Et | H | |
| 104 | NMeCH₂cPr | Et | Et | H | |
| 105 | NMe(CH₂)₂OH | Et | Et | H | |
| 106 | NMe(CH₂)₂OMe | Et | Et | H | |
| 107 | NMe(CH₂)₂OEt | Et | Et | H | |
| 108 | NMeCHMeCH₂OMe | Et | Et | H | |
| 109 | NMeCHMeCH₂OEt | Et | Et | H | |
| 110 | NMe(CH₂)₃OMe | Me | Me | SO₂n-Pr | |
| 111 | NHEt | Me | Me | SO₂n-Pr | |
| 112 | NH(n-Pr) | Me | Me | SO₂n-Pr | |
| 113 | NH(n-Bu) | Me | Me | SO₂n-Pr | |
| 114 | NHCH₂CH=CH₂ | Me | Me | SO₂n-Pr | |
| 115 | NHCH₂C≡CH | Me | Me | SO₂n-Pr | |
| 116 | NHCH₂cPr | Me | Me | SO₂n-Pr | |
| 117 | NH(CH₂)₂OH | Me | Me | SO₂n-Pr | |
| 118 | NH(CH₂)₂OMe | Me | Me | SO₂n-Pr | 0.65(m, 2H), 0.85(m, 2H), 1.1(t, 3H), 1.58(m, 1H), 1.95(m, 2H), 2.3(s, 3H), 3.18(s, 3H), 3.3(m, 2H), 3.4(m, 2H), 3.4(s, 3H), 3.6(m, 2H), 3.78(s, 3H), 7.0(d, 1H), 7.8(d, 1H) |
| 119 | NH(CH₂)₂OEt | Me | Me | SO₂n-Pr | |
| 120 | NHCHMeCH₂OMe | Me | Me | SO₂n-Pr | |
| 121 | NHCHMeCH₂OEt | Me | Me | SO₂n-Pr | |
| 122 | NH(CH₂)₃OMe | Me | Me | SO₂n-Pr | |
| 123 | pyrrolidinyl | Me | Me | SO₂n-Pr | |
| 124 | piperidinyl | Me | Me | SO₂n-Pr | |
| 125 | NMe₂ | Me | Me | SO₂n-Pr | |
| 126 | NMeEt | Me | Me | SO₂n-Pr | |
| 127 | NMe(n-Pr) | Me | Me | SO₂n-Pr | |
| 128 | NMe(n-Bu) | Me | Me | SO₂n-Pr | |
| 129 | NMeCH₂CH=CH₂ | Me | Me | SO₂n-Pr | |
| 130 | NMeCH₂C≡CH | Me | Me | SO₂n-Pr | |
| 131 | NMeCH₂cPr | Me | Me | SO₂n-Pr | |
| 132 | NMe(CH₂)₂OH | Me | Me | SO₂n-Pr | |
| 133 | NMe(CH₂)₂OMe | Me | Me | SO₂n-Pr | |
| 134 | NMe(CH₂)₂OEt | Me | Me | SO₂n-Pr | |
| 135 | NMeCHMeCH₂OMe | Me | Me | SO₂n-Pr | |
| 136 | NMe(CH₂)₃OMe | Me | Me | SO₂n-Pr | |
| 137 | NHMe | Me | Me | SO₂-(4-Me—Ph) | |
| 138 | NHEt | Me | Me | SO₂-(4-Me—Ph) | |
| 139 | NH(n-Pr) | Me | Me | SO₂-(4-Me—Ph) | |
| 140 | NH(n-Bu) | Me | Me | SO₂-(4-Me—Ph) | |
| 141 | NHCH₂CH=CH₂ | Me | Me | SO₂-(4-Me—Ph) | |
| 142 | NHCH₂C≡CH | Me | Me | SO₂-(4-Me—Ph) | |
| 143 | NHCH₂cPr | Me | Me | SO₂-(4-Me—Ph) | |
| 144 | NH(CH₂)₂OH | Me | Me | SO₂-(4-Me—Ph) | |
| 145 | NH(CH₂)₂OMe | Me | Me | SO₂-(4-Me—Ph) | 0.82(m, 2H), 0.9(m, 2H), 2.08(m, 1H), 2.32(s, 3H), 2.45(s, 3H), 3.18(s, 3H), 3.38(t, 2H), 3.4(s, 3H), 3.6(t, 2H), 3.6 (s, 3H), 6.9(d, 1H), 7.35(d, 2H), 7.5 (d, 2H), 7.65(d, 1H) |
| 146 | N NH(CH₂)₂OEt | Me | Me | SO₂-(4-Me—Ph) | |
| 147 | NHCHMeCH₂OMe | Me | Me | SO₂-(4-Me—Ph) | |
| 148 | NHCHMeCH₂OEt | Me | Me | SO₂-(4-Me—Ph) | |
| 149 | NH(CH₂)₃OMe | Me | Me | SO₂-(4-Me—Ph) | |

TABLE A-continued

| No. | NR¹R² | R³ | R⁴ | R⁵ | ¹H-NMR: δ[CDCl₃] |
|---|---|---|---|---|---|
| 150 | pyrrolidinyl | Me | Me | SO₂-(4-Me—Ph) | |
| 151 | piperidinyl | Me | Me | SO₂-(4-Me—Ph) | |
| 152 | NMe₂ | Me | Me | SO₂-(4-Me—Ph) | |
| 153 | NMeEt | Me | Me | SO₂-(4-Me—Ph) | |
| 154 | NMe(n-Pr) | Me | Me | SO₂-(4-Me—Ph) | |
| 155 | NMe(n-Bu) | Me | Me | SO₂-(4-Me—Ph) | |
| 156 | NMeCH₂CH=CH₂ | Me | Me | SO₂-(4-Me—Ph) | |
| 157 | NMeCH₂C≡CH | Me | Me | SO₂-(4-Me—Ph) | |
| 158 | NMeCH₂cPr | Me | Me | SO₂-(4-Me—Ph) | |
| 159 | NMe(CH₂)₂OH | Me | Me | SO₂-(4-Me—Ph) | |
| 160 | NMe(CH₂)₂OMe | Me | Me | SO₂-(4-Me—Ph) | |
| 161 | NMe(CH₂)₂OEt | Me | Me | SO₂-(4-Me—Ph) | |
| 162 | NMeCHMeCH₂OMe | Me | Me | SO₂-(4-Me—Ph) | |
| 163 | NMe(CH₂)₃OMe | Me | Me | SO₂-(4-Me—Ph) | |
| 164 | NHMe | Me | Me | CH₂-(2,6-F₂—Ph) | |
| 165 | NHEt | Me | Me | CH₂-(2,6-F₂—Ph) | |
| 166 | NH(n-Pr) | Me | Me | CH₂-(2,6-F₂—Ph) | |
| 167 | NH(n-Bu) | Me | Me | CH₂-(2,6-F₂—Ph) | |
| 168 | NHCH₂CH=CH₂ | Me | Me | CH₂-(2,6-F₂—Ph) | |
| 169 | NHCH₂C≡CH | Me | Me | CH₂-(2,6-F₂—Ph) | |
| 170 | NHCH₂cPr | Me | Me | CH₂-(2,6-F₂—Ph) | |
| 171 | NH(CH₂)₂OH | Me | Me | CH₂-(2,6-F₂—Ph) | |
| 172 | NH(CH₂)₂OMe | Me | Me | CH₂-(2,6-F₂—Ph) | 0.58(m, 2H), 0.78(m, 2H), 1.42 (m, 1H), 2.32(s, 3H), 3.18(s, 3H), 3.4 (t, 2H), 3.4(s, 3H), 3.42(s, 2H), 3.6 (t, 2H), 6.92(m, 2H), 7.02(d, 1H), 7.35 (m, 1H), 7.8(d, 1H) |
| 173 | NH(CH₂)₂OEt | Me | Me | CH₂-(2,6-F₂—Ph) | |
| 174 | NHCHMeCH₂OMe | Me | Me | CH₂-(2,6-F₂—Ph) | |
| 175 | NHCHMeCH₂OEt | Me | Me | CH₂-(2,6-F₂—Ph) | |
| 176 | NH(CH₂)₃OMe | Me | Me | CH₂-(2,6-F₂—Ph) | |
| 177 | pyrrolidinyl | Me | Me | CH₂-(2,6-F₂—Ph) | |
| 178 | piperidinyl | Me | Me | CH₂-(2,6-F₂—Ph) | |
| 179 | NMe₂ | Me | Me | CH₂-(2,6-F₂—Ph) | |
| 180 | NMeEt | Me | Me | CH₂-(2,6-F₂—Ph) | |
| 181 | NMe(n-Pr) | Me | Me | CH₂-(2,6-F₂—Ph) | |
| 182 | NMe(n-Bu) | Me | Me | CH₂-(2,6-F₂—Ph) | |
| 183 | NMeCH₂CH=CH₂ | Me | Me | CH₂-(2,6-F₂—Ph) | |
| 184 | NMeCH₂C≡CH | Me | Me | CH₂-(2,6-F₂—Ph) | |
| 185 | NMeCH₂cPr | Me | Me | CH₂-(2,6-F₂—Ph) | |
| 186 | NMe(CH₂)₂OH | Me | Me | CH₂-(2,6-F₂—Ph) | |
| 187 | NMe(CH₂)₂OMe | Me | Me | CH₂-(2,6-F₂—Ph) | |
| 188 | NMe(CH₂)₂OEt | Me | Me | CH₂-(2,6-F₂—Ph) | |
| 189 | NMeCHMeCH₂OMe | Me | Me | CH₂-(2,6-F₂—Ph) | |
| 190 | NMe(CH₂)₃OMe | Me | Me | CH₂-(2,6-F₂—Ph) | |
| 191 | NH(c-Pr) | Me | Me | H | 0.48-0.64(m, 4H), 0.74-0.82(m, 4H), 1.05(m, 1H), 2.48(s, 3H), 2.83(m, 1H), 2.98(s, 3H), 3.61(s, 3H), 6.89(d, 1H), 7.76(d, 1H) |

TABLE A-continued

| No. | NR¹R² | R³ | R⁴ | R⁵ | ¹H-NMR: δ[CDCl₃] |
|---|---|---|---|---|---|
| 192 | NH(i-Pr) | Me | Me | H | 0.53(m, 2H), 0.78(m, 2H), 1.02 (m, 1H), 1.22(d, 6H), 2.27(s, 3H), 3.10 (s, 3H), 3.60(s, 3H), 3.77(m, 1H), 6.96 (d, 1H), 7.82(d, 1H) |
| 193 | NH(i-Bu) | Me | Me | H | 0.54(m, 2H), 0.78(m, 2H), 1.01 (m, 1H), 1.04(d, 6H), 1.94(m, 1H), 2.30 (s, 3H), 3.02(d, 2H), 3.07(s, 3H), 3.61 (s, 3H), 6.97(d, 1H), 7.80(d, 1H) |
| 194 | NH(s-Bu) | Me | Me | H | 0.54(m, 2H), 0.78(m, 2H), 0.95-1.06 (m, 4H), 1.15(d, 3H), 1.49(m, 1H), 1.64 (m, 1H), 2.27(s, 3H), 3.08(s, 3H), 3.56 (m, 1H), 3.61(s, 3H), 6.94(d, 1H), 7.79 (d, 1H) |
| 195 | NH(c-Pentyl) | Me | Me | H | 0.53(m, 2H), 0.77(m, 2H), 1.03 (m, 1H), 1.46-1.67(m, 4H), 1.69-1.85 (m, 2H), 1.88-2.01(m, 2H), 2.32(s, 3H), 3.07(s, 3H), 3.60(s, 3H), 3.96(m, 1H), 6.90(d, 1H), 7.78(d, 1H) |
| 196 | NH-Bzl | Me | Me | H | 0.54(m, 2H), 0.78(m, 2H), 0.98 (m, 1H), 2.40(s, 3H), 2.70(s, 3H), 3.61 (s, 3H), 4.38(s, 2H), 7.03(d, 1H), 7.24-7.38 (m, 5H), 7.80(d, 1H) |
| 197 | NH(CH₂)₂OAc | Me | Me | H | 0.54(m, 2H), 0.78(m, 2H), 0.98 (m, 1H), 2.12(s, 3H), 2.32(s, 3H), 3.14 (s, 3H), 3.47(m, 2H), 3.61(s, 3H), 4.32 (m, 2H), 7.06(d, 1H), 7.84(d, 1H) |
| 198 | NH(CH₂)₂O(i-Pr) | Me | Me | H | 0.54(m, 2H), 0.77(m, 2H), 1.00 (m, 1H), 1.22(d, 6H), 2.30(s, 3H), 3.18 (s, 3H), 3.37(m, 2H), 3.60(s, 3H), 3.62-3.73 (m, 3H), 6.99(d, 1H), 7.83(d, 1H) |
| 199 | NHCH(Me)(c-Pr) | Me | Me | H | 0.10-0.24(m, 2H), 0.38-0.59(m, 4H), 0.77(m, 2H), 0.91-1.05(m, 2H), 1.24 (d, 3H), 2.23(s, 3H), 3.00(m, 1H), 3.16 (s, 3H), 3.60(s, 3H), 6.97(d, 1H), 7.81 (d, 1H) |
| 200 | NHCH(Et)(c-Pr) | Me | Me | H | 0.02(m, 1H), 0.21(m, 1H), 0.34 (m, 1H), 0.48-0.60(m, 3H), 0.78 (m, 2H), 0.91(m, 1H), 0.98-1.11 (m, 4H), 1.69(m, 2H), 2.22(s, 3H), 2.75 (m, 1H), 3.16(s, 3H), 3.62(s, 3H), 6.95 (d, 1H), 7.80(d, 1H) |
| 201 | 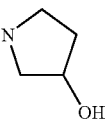 | Me | Me | H | 0.52(m, 2H), 0.78(m, 2H), 0.91M (m, 1H), 2.03-2.15(m, 1H), 2.18-2.35 (m, 1H), 2.32(s, 3H), 3.28(s, 3H), 3.31-3.42 (m, 2H), 3.46-3.58(m, 2H), 3.61 (s, 3H), 4.58(m, 1H), 7.36(d, 1H), 8.02 (d, 1H) |
| 202 | 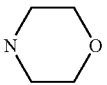 | Me | Me | H | 0.49(m, 2H), 0.78(m, 2H), 0.89 (m, 1H), 2.46(s, 3H), 2.97(m, 2H), 3.35 (s, 3H), 3.55-3.66(m, 2H), 3.62(s, 3H), 3.80-3.97(m, 4H), 7.36(d, 1H), 8.06 (d, 1H) |
| 203 | 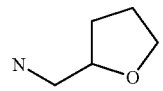 | Me | Me | H | 0.54(m, 2H), 0.77(m, 2H), 0.99 (m, 1H), 1.59-1.73(m, 1H), 1.88-2.12 (m, 3H), 2.30(s, 3H), 3.18(m, 1H), 3.22 (s, 3H), 3.41(m, 1H), 3.60(s, 3H), 3.74-3.84 (m, 1H), 3.87-3.96(m, 1H), 4.05 (m, 1H), 6.98(d, 1H), 7.83(d, 1H) |
| 204 | 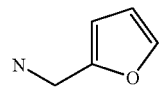 | Me | Me | H | 0.53(m, 2H), 0.78(m, 2H), 1.01 (m, 1H), 2.38(s, 3H), 2.86(s, 3H), 3.61 (s, 3H), 4.39(s, 2H), 6.23(m, 1H), 6.31 (m, 1H), 7.03(d, 1H), 7.33(m, 1H), 7.82 (d, 1H) |

TABLE A-continued

[Structure: pyrazole-cyclopropyl ketone linked to benzene ring with CH3, NR1R2, OR5, SO2R3 substituents]

| No. | NR¹R² | R³ | R⁴ | R⁵ | ¹H-NMR: δ[CDCl₃] |
|---|---|---|---|---|---|
| 205 | N(Me)(CH₂-tetrahydrofuran-2-yl) | Me | Me | H | |
| 206 | pyrrol-1-yl | Me | Me | H | 0.58(m, 2H), 0.82(m, 2H), 0.97 (m, 1H), 1.99(s, 3H), 2.62(s, 3H), 3.61 (s, 3H), 6.41(m, 2H), 6.78(m, 2H), 7.58 (d, 1H), 8.18(d, 1H) |
| 207 | pyrazol-1-yl | Me | Me | H | 0.60(b, 2H), 0.82(b, 2H), 0.99(m, 1H), 1.95(s, 3H), 2.88(s, 3H), 3.61(s, 3H), 6.57(m, 1H), 7.67(d, 1H), 7.71(d, 1H), 7.82(d, 1H), 8.17(d, 1H) |
| 208 | 5-Me-pyrazol-1-yl | Me | Me | H | 0.44-0.90(m, 4H), 1.03(m, 1H), 1.98 (s, 3H), 2.41(s, 3H), 2.89(s, 3H), 3.62 (s, 3H), 6.38(d, 1H), 7.62(d, 1H), 7.67 (d, 1H), 8.17(d, 1H) |
| 209 | 4-Me-pyrazol-1-yl | Me | Me | H | 0.60(b, 2H), 0.82(b, 2H), 1.00(m, 1H), 1.96(s, 3H), 2.22(s, 3H), 2.89(s, 3H), 3.62(s, 3H), 7.48(s, 1H), 7.64(s, 1H), 7.66(d, 1H), 8.16(d, 1H) |
| 210 | 4-CF₃-pyrazol-1-yl | Me | Me | H | 0.50-0.69(m, 2H), 0.84(m, 2H), 0.96 (m, 1H), 1.98(s, 3H), 2.97(s, 3H), 3.63 (s, 3H), 7.71(d, 1H), 7.98(s, 1H), 8.01 (s, 1H), 8.19(d, 1H) |
| 211 | 4-OMe-pyrazol-1-yl | Me | Me | H | 0.59(b, 2H), 0.82(b, 2H), 0.97(m, 1H), 1.98(s, 3H), 2.93(s, 3H), 3.62(s, 3H), 3.83(s, 3H), 7.36(s, 1H), 7.57(s, 1H), 7.64(d, 1H), 8.16(d, 1H) |
| 212 | 3,5-diMe-pyrazol-1-yl | Me | Me | H | 0.48-0.81(m, 3H), 0.88(m, 1H), 1.04 (m, 1H), 1.92(s, 3H), 2.08(s, 3H), 2.35 (s, 3H), 3.08(s, 3H), 3.62(s, 3H), 6.11 (s, 1H), 7.70(d, 1H), 8.18(d, 1H) |
| 213 | 3-Me-4-CF₃-pyrazol-1-yl | Me | Me | H | 0.56(b, 1H), 0.64(b, 1H), 0.84(b, 2H), 0.96(m, 1H), 2.01(s, 3H), 2.44(s, 3H), 2.98(s, 3H), 3.61(s, 3H), 7.68(d, 1H), 7.86(s, 1H), 8.16(d, 1H) |

B. FORMULATION EXAMPLES

1. Dust

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of a compound of the formula (I), 64 parts by weight of kaolin-containing quartz as inert substance, 10 parts by weight of potassium ligninsulfonate and 1 part by weight of sodium oleoylmethyltaurate as wetter and dispersant, and grinding the mixture in a pinned-disk mill.

3. Dispersion Concentrate

A dispersion concentrate which is readily dispersible in water is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of oxethylated nonylphenol as emulsifier.

5. Water-dispersible Granules

Water-dispersible granules are obtained by mixing
75 parts by weight of a compound of the formula (I),
10 " calcium ligninsulfonate,
5 " sodium lauryl sulfate,
3 " polyvinyl alcohol and
7 " kaolin, grinding the mixture in a pinned-disk mill and granulating the powder in a fluidized bed by spraying on water as granulation liquid.

Water-dispersible granules are also obtained by homogenizing and precomminuting, in a colloid mill, 25 parts by weight of a compound of the formula (I),
5 " sodium 2,2'-dinaphthylmethane-6,6'-disulfonate,
2 " sodium oleoylmethyltaurate,
1 " polyvinyl alcohol,
17 " calcium carbonate and
50 " water, subsequently grinding the mixture in a bead mill, and atomizing and drying the resulting suspension in a spray tower by means of a single-fluid nozzle.

C. BIOLOGICAL EXAMPLES

1. Pre-emergence Action Against Harmful Plants or Damage of Crop Plants

Seeds of monocotyledonous and dicotyledonous harmful plants and seeds of corn, soybean and wheat are placed into sandy loam in cardboard pots and covered with soil. The compounds according to the invention and the prior-art compounds, formulated as wettable powders or emulsion concentrates, are then applied to the surface of the covering soil as an aqueous suspension or emulsion at an application rate of 600 to 800 l of water/ha (converted) in one of the dosages given in tables 1 to 10. After the treatment, the pots are placed in a greenhouse and kept under good growth conditions for the harmful plants and crop plants. Visual scoring of plant or emergence damage is carried out after the test plants have emerged after an experimental period of 3 to 4 weeks. It is found that the compounds according to the invention, having the same or better herbicidal activity, cause less damage to the crop plants than the compounds known from the prior art (comparative tables 1 to 4, 6 to 10).

2. Post-emergence Action Against Harmful Plants or Damage of Crop Plants

Seeds of monocotyledonous and dicotyledonous harmful plants and seeds of corn, soybean and wheat are placed into sandy loam in cardboard pots, covered with soil and grown in the greenhouse under good growth conditions. Two to three weeks after sowing the harmful plants and the crop plants are treated in the three-leaf stage. The compounds according to the invention and the prior-art compounds, formulated as wettable powders or emulsion concentrates, are sprayed onto the green plant parts at an application rate of 600 to 800 l of water/ha (converted) in one of the dosages given in tables 1 to 10. After the test plants have remained in the greenhouse under optimum growth conditions for 3 to 4 weeks, the effect of the compounds is rated in comparison to compounds disclosed in the prior art. It is found that the compounds according to the invention, having the same or better herbicidal activity, cause less damage to the crop plants than the compounds known from the prior art (comparative tables 1 to 4, 6 to 10).

3. Action Against Harmful Plants or Damage of Rice

Rice plants and harmful plants typical in rice crops are grown in the greenhouse under paddy rice conditions (water level: 2-3 cm). After the treatment with the compounds according to the invention and the prior-art compounds, the test plants are placed in the greenhouse under optimum growth conditions and kept like this during the entire test. About three weeks after the application, evaluation is carried out by visual scoring of the damage to the plants. It is found that the compounds according to the invention, having the same or better herbicidal activity, cause less damage to the rice plants than the compounds known from the prior art (comparative tables 2 and 5).

TABLE B

Compounds according to the invention

Structure

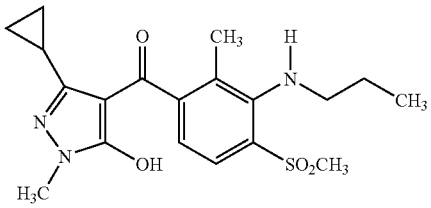

No. 3. of Table A

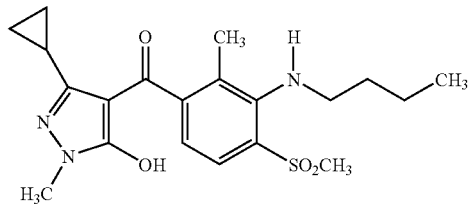

No. 4 of Table A

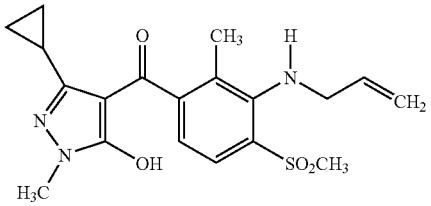

No. 5 of Table A

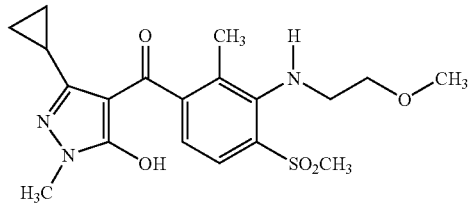

No. 9 of Table A

TABLE B-continued

Compounds according to the invention

Structure

No. 10 of Table A

No. 14 of Table A

No. 15 of Table A

TABLE C

Prior-art compounds

Structure

S1

S2

S3

S4

S5

S6

S7

The abbreviations used in the comparative tables below denote:

(harmful plants)

| | | | |
|---|---|---|---|
| AVEFA | Avena fatua | DIGSA | Digitaria sanguinalis |
| ECHCG | Echinochloa crus galli | GALAP | Galium aparine |
| MATIN | Matricaria inodora | PHBPU | Pharbitis purpureum |
| SETVI | Setaria viridis | STEME | Stellaria media |
| VERPE | Veronica persica | VIOTR | Viola tricolor |
| | | | (crop plants) |
| GLXMA | Glycine max (soybean) | ORYSA | Oryza sativa (rice) |
| TRZAS | Triticum aestivum (wheat) | ZEAMX | Zea mays (corn) |

COMPARATIVE TABLE 1

Post-emergence application

| Compound | Dosage [g of a.i./ha] | Herbicidal action | | | | Damage to the crop plants |
|---|---|---|---|---|---|---|
| | | DIGSA | ECHCG | MATIN | VIOTR | ZEAMX |
| No. 3 | 80 | 90% | 90% | 70% | 90% | 30% |
| S2 | 80 | 80% | 80% | 30% | 80% | 60% |

COMPARATIVE TABLE 2

| | | Post-emergence application | | | |
| --- | --- | --- | --- | --- | --- |
| | Dosage | Herbicidal action | | Damage to the crop plants | |
| Compound | [g of a.i./ha] | GALAP | VERPE | GLXMA | ORYSA |
| No. 4 | 20 | 80% | 60% | 0% | 0% |
| S3 | 20 | 40% | 20% | 20% | 30% |

COMPARATIVE TABLE 3

| | | Post-emergence application | | | | |
| --- | --- | --- | --- | --- | --- | --- |
| Com-pound | Dosage [g of a.i./ha] | Herbicidal action | | | Damage to the crop plants | |
| | | GALAP | MATIN | STEME | GLXMA | ZEAMX |
| No. 5 | 80 | 80% | 50% | 100% | 0% | 10% |
| S4 | 80 | 80% | 30% | 100% | 50% | 30% |

COMPARATIVE TABLE 4

| | | Post-emergence application | | |
| --- | --- | --- | --- | --- |
| | Dosage | Herbicidal action | | Damage to crop plants |
| Compound | [g of a.i./ha] | MATIN | STEME | ZEAMX |
| No. 15 | 80 | 60% | 70% | 0% |
| S5 | 80 | 40% | 20% | 10% |

COMPARATIVE TABLE 5

| | | Post-emergence application | |
| --- | --- | --- | --- |
| Compound | Dosage [g of a.i./ha] | Herbicidal action SETVI | Damage to the crop plants ORYSA |
| No. 14 | 320 | 100% | 10% |
| S6 | 320 | 90% | 20% |

COMPARATIVE TABLE 6

| | | Post-emergence application | | | |
| --- | --- | --- | --- | --- | --- |
| | Dosage | Herbicidal action | | Damage to the crop plants | |
| Compound | [g of a.i./ha] | ECHCG | MATIN | GLXMA | TRZAS |
| No. 14 | 320 | 80% | 50% | 10% | 0% |
| S6 | 320 | 50% | 0% | 20% | 10% |

COMPARATIVE TABLE 7

| | | Pre-emergence application | |
| --- | --- | --- | --- |
| Compound | Dosage [g of a.i./ha] | Herbicidal action GALAP | Damage to the crop plants ZEAMX |
| No. 9 | 320 | 80% | 0% |
| S7 | 320 | 70% | 20% |

COMPARATIVE TABLE 8

| | | Post-emergence application | | | |
| --- | --- | --- | --- | --- | --- |
| | Dosage | Herbicidal action | | Damage to the crop plants | |
| Compound | [g of a.i./ha] | AVEFA | MATIN | GLXMA | ZEAMX |
| No. 9 | 320 | 70% | 80% | 20% | 0% |
| S7 | 320 | 50% | 70% | 60% | 20% |

COMPARATIVE TABLE 9

| | | Post-emergence application | | | |
| --- | --- | --- | --- | --- | --- |
| | Dosage | Herbicidal action | | | Damage to the crop plants |
| Compound | [g of a.i./ha] | MATIN | PHBPU | VERPE | GLXMA |
| No. 10 | 320 | 100% | 100% | 100% | 20% |
| S1 | 320 | 60% | 90% | 100% | 90% |

COMPARATIVE TABLE 10

| | | Post-emergence application | | | | | |
| --- | --- | --- | --- | --- | --- | --- | --- |
| | Dosage | Herbicidal action | | | | Damage to the crop plants | |
| Compound | [g of a.i./ha] | ECHCG | MATIN | PHBPU | VERPE | GLXMA | ZEAMX |
| No. 10 | 320 | 100% | 100% | 100% | 100% | 20% | 0% |
| S7 | 320 | 90% | 70% | 40% | 90% | 60% | 20% |

What is claimed is:

1. A compound of the formula (I) or salt thereof

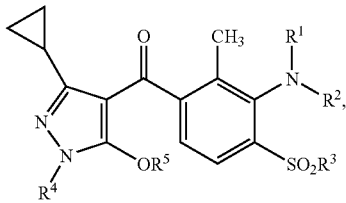

in which
R$^1$ and R$^2$ independently of one another are hydrogen, furan-2-yl, tetrahydrofuran-2-yl-methyl,
or (C$_1$-C$_4$)-alkyl, (C$_3$-C$_4$)-alkenyl, (C$_3$-C$_4$)-alkynyl, (C$_3$-C$_6$)-cycloalkyl, (C$_3$-C$_6$)-cycloalkenyl, (C$_3$-C$_6$)-cycloalkyl-(C$_1$-C$_4$)-alkyl or (C$_3$-C$_6$)-cycloalkenyl-(C$_1$-C$_4$)-alkyl substituted by m radicals from the group consisting of fluorine, chlorine, bromine, cyano, hydroxyl, (C$_1$-C$_4$)-alkyl, (C$_1$-C$_4$)-alkoxy and (C$_1$-C$_4$)-alkoxy-(C$_1$-C$_4$)-alkoxy, where R$^1$ and R$^2$ are not simultaneously hydrogen,
or
NR$^1$R$^2$ is a 4- to 7-membered saturated, partially saturated, fully unsaturated or aromatic ring comprising as ring atoms n heteroatoms from the group consisting of nitrogen, oxygen and sulfur which ring is substituted by m radicals from the group consisting of fluorine, chlorine, bromine, iodine, cyano, hydroxyl, trifluoromethyl, nitro, (C$_1$-C$_4$)-alkyl, (C$_1$-C$_4$)-alkoxy, fluoro-(C$_1$-C$_3$)-alkyl, fluoro-(C$_1$-C$_3$)-alkoxy or (C$_1$-C$_3$)-alkoxymethyl;
R$^3$ is methyl, ethyl or isopropyl;
R$^4$ is (C$_1$-C$_4$)-alkyl, (C$_3$-C$_4$)-alkenyl or (C$_3$-C$_4$)-alkynyl;
R$^5$ is hydrogen, (C$_1$-C$_4$)-alkylsulfonyl, (C$_3$-C$_4$)-alkenylsulfonyl, (C$_3$-C$_4$)-alkynylsulfonyl,
or phenylsulfonyl or benzyl substituted by m radicals from the group consisting of fluorine, chlorine, bromine, cyano, trifluoromethyl, nitro, methyl, ethyl, methoxy and ethoxy,
m is 0, 1, 2 or 3;
n is 1, 2 or 3.

2. The compound as claimed in claim 1 in which
R$^1$ and R$^2$ independently of one another are hydrogen,
or (C$_1$-C$_4$-alkyl, (C$_3$-C$_4$)-alkenyl, (C$_3$-C$_4$-alkynyl, (C$_3$-C$_6$)-cycloalkyl, (C$_3$-C$_6$)-cycloalkenyl, (C$_3$-C$_6$)-cycloalkyl-(C$_1$-C$_4$)-alkyl or (C$_3$-C$_6$)-cycloalkenyl-(C$_1$-C$_4$)-alkyl substituted by m radicals from the group consisting of fluorine, chlorine, bromine, cyano, hydroxyl, (C$_1$-C$_4$)-alkyl, (C$_1$-C$_4$)-alkoxy and (C$_1$-C$_4$)-alkoxy-(C$_1$-C$_4$)-alkoxy, where R$^1$ and R$^2$ are not simultaneously hydrogen,
or
NR$^1$R$^2$ is a 4- to 7-membered saturated, partially saturated, fully unsaturated or aromatic ring comprising as ring atoms n heteroatoms from the group consisting of nitrogen, oxygen and sulfur which ring is substituted by m radicals from the group consisting of fluorine, chlorine, bromine, iodine, cyano, trifluoromethyl, nitro, (C$_1$-C$_4$)-alkyl, (C$_1$-C$_4$)-alkoxy, fluoro-(C$_1$-C$_3$)-alkyl, fluoro-(C$_1$-C$_3$)-alkoxy or (C$_1$-C$_3$)-alkoxymethyl.

3. The compound as claimed in claim 1 in which
R$^1$ and R$^2$ independently of one another are hydrogen, methyl, butyl, ethyl, propyl, propenyl, propynyl, cyclopropyl, cyclopropylmethyl, methoxyethyl, methoxypropyl, 2-methoxy-1-methylethyl, 2-ethoxy-1-methylethyl, hydroxyethyl or ethoxyethyl,
or
NR$^1$R$^2$ form a radical from the group consisting of 1-pyrrolyl, 1-pyrrolidinyl, 1-pyrazolyl, 1-piperidine, 1-morpholinyl and 1-piperazinyl which is substituted by m radicals from the group consisting of fluorine, chlorine, bromine, iodine, cyano, trifluoromethyl, (C$_1$-C$_4$)-alkyl and (C$_1$-C$_4$)-alkoxy.

4. The compound as claimed in claim 1 in which
R$^1$ and R$^2$ independently of one another are hydrogen, methyl, butyl, ethyl, propyl, propenyl, propynyl, cyclopropyl, cyclopropylmethyl, methoxyethyl, methoxypropyl, 2-methoxy-1-methylethyl, 2-ethoxy-1-methylethyl, hydroxyethyl or ethoxyethyl,
or
NR$^1$R$^2$ form a radical from the group consisting of 1-pyrrolyl, 1-pyrrolidinyl, 1-pyrazolyl, 1-piperidine, 1-morpholinyl and 1-piperazinyl and
R$^5$ is hydrogen, propylsulfonyl, tosyl or 2,6-difluorobenzyl.

5. The compound as claimed in claim 1 in which
R$^3$ is methyl or ethyl;
R$^4$ is methyl or ethyl, and
R$^5$ is hydrogen.

* * * * *